(12) United States Patent
Heller

(10) Patent No.: US 7,927,882 B2
(45) Date of Patent: *Apr. 19, 2011

(54) INSTRUMENT

(75) Inventor: Zindel Herbert Heller, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1146 days.

This patent is subject to a terminal disclaimer.

(21) Appl. No.: 11/199,488

(22) Filed: Aug. 8, 2005

(65) Prior Publication Data

US 2006/0035384 A1   Feb. 16, 2006

Related U.S. Application Data

(63) Continuation of application No. 10/046,030, filed on Nov. 7, 2001, now Pat. No. 7,018,843.

(51) Int. Cl.
*G01N 33/48* (2006.01)

(52) U.S. Cl. .............. 436/95; 436/63; 436/70; 436/149; 436/150; 422/67; 422/68.1; 422/82.01; 435/14

(58) Field of Classification Search ............ 436/63, 436/70, 95, 149, 150; 422/67, 68.1, 73, 82.01; 435/14

See application file for complete search history.

(56) References Cited

U.S. PATENT DOCUMENTS

| | | | |
|---|---|---|---|
| 3,250,987 A | 5/1966 | Okada et al. |
| 3,648,159 A | 3/1972 | Stansell et al. |
| 3,770,607 A | 11/1973 | Williams |
| 3,838,033 A | 9/1974 | Mindt et al |
| 3,902,970 A | 9/1975 | Levin |
| 3,925,183 A | 12/1975 | Oswin et al. |
| 3,937,615 A | 2/1976 | Clack et al. |
| 4,005,002 A | 1/1977 | Racine et al. |
| 4,040,908 A | 8/1977 | Clark, Jr. |
| 4,086,631 A | 4/1978 | Vick |
| 4,123,701 A | 10/1978 | Josefsen et al. |
| 4,127,448 A | 11/1978 | Schick et al. |
| 4,214,968 A | 7/1980 | Battaglia et al. |
| 4,217,196 A | 8/1980 | Huch |
| 4,224,125 A | 9/1980 | Nakamura et al. |
| 4,225,410 A | 9/1980 | Pace |
| 4,230,537 A | 10/1980 | Delente et al. |
| 4,260,680 A | 4/1981 | Muramatsu et al. |
| 4,263,343 A | 4/1981 | Kim |
| 4,265,250 A | 5/1981 | Parker |
| 4,273,134 A | 6/1981 | Ricciardelli |
| 4,301,412 A | 11/1981 | Hill et al. |
| 4,303,887 A | 12/1981 | Hill et al. |
| 4,366,033 A | 12/1982 | Richter et al. |
| 4,407,959 A | 10/1983 | Tsuji et al. |
| 4,413,628 A | 11/1983 | Tamulis |
| 4,420,564 A | 12/1983 | Tsuji et al. |
| 4,431,004 A | 2/1984 | Bessman et al. |
| 4,436,094 A | 3/1984 | Cerami |
| 4,440,175 A | 4/1984 | Wilkins |
| 4,477,314 A | 10/1984 | Richter et al. |
| 4,477,575 A | 10/1984 | Vogel et al. |
| 4,499,423 A | 2/1985 | Matthiessen |
| 4,517,291 A | 5/1985 | Seago |
| 4,547,735 A | 10/1985 | Kiesewetter et al. |
| 4,654,197 A | 3/1987 | Lilja et al. |
| 4,671,288 A | 6/1987 | Gough |
| 4,679,562 A | 7/1987 | Luksha |
| 4,682,602 A | 7/1987 | Prohaska |
| 4,703,756 A | 11/1987 | Gough et al. |
| 4,711,245 A | 12/1987 | Higgins et al. |
| 4,734,184 A | 3/1988 | Burleigh et al. |
| 4,750,496 A | 6/1988 | Reinhart et al. |
| 4,759,828 A | 7/1988 | Young et al. |
| 4,789,804 A | 12/1988 | Karube et al. |
| 4,795,542 A | 1/1989 | Ross et al. |
| 4,805,624 A | 2/1989 | Yao et al. |
| 4,816,224 A | 3/1989 | Vogel et al. |
| 4,820,399 A | 4/1989 | Senda et al. |
| 4,871,258 A | 10/1989 | Herpichboehm et al. |
| 4,894,137 A | 1/1990 | Takizawa et al. |
| 4,897,162 A | 1/1990 | Lewandowski et al. |
| 4,897,173 A | 1/1990 | Nankai et al. |

(Continued)

FOREIGN PATENT DOCUMENTS

DE    3228542    2/1984

(Continued)

OTHER PUBLICATIONS

Talbott, et al, "A New Microchemical Approach to Amperometric Analysis," Microchemical Journal, vol. 37, pp. 5-12 (1988).

Morris, et al, "An Electrochemical Capillary Fill Device for the Analysis of Glucose Incorporating Glucose Oxidase and Ruthenium(III) Hexamine as Mediator," Electroanalysis, vol. 4, pp. 1-9 (1992).

Cass, et al, "Ferrocene-Mediated Enzyme Electrode for Amperometric Determination of Glucose," Anal. Chem., vol. 56, pp. 667-671 (1984).

Zhao, "Contributions of Suspending Medium to Electrical Impedance of Blood," Biochimica et Biophysica Acta, vol. 1201, pp. 179-185 (1994).

Zhao, "Electrical Impedance and Haematocrit of Human Blood with Various Anticoagulants," Physiol. Meas., vol. 14, pp. 299-307 (1993).

(Continued)

*Primary Examiner* — Maureen M Wallenhorst

(74) *Attorney, Agent, or Firm* — Barnes & Thornburg LLP

(57) ABSTRACT

A method and apparatus for performing a first measurement on a biological fluid or control, which first measurement varies with both the concentration of a first component and at least one of the presence and concentration of a second component. The method and apparatus perform a second measurement on the biological fluid or control, which second measurement varies primarily only with the at least one of the presence and concentration of the second component to develop an indication of the at least one of the presence and concentration of the second component. The first and second measurements may be made sequentially or simultaneously. The method and apparatus then remove an amount representative of the indicated presence or concentration of the second component from the concentration of the first component indicated by the first measurement.

54 Claims, 7 Drawing Sheets

U.S. PATENT DOCUMENTS

| | | | |
|---|---|---|---|
| 4,919,770 | A | 4/1990 | Preidel et al. |
| 4,927,516 | A | 5/1990 | Yamaguchi et al. |
| 4,935,106 | A | 6/1990 | Liston et al. |
| 4,938,860 | A | 7/1990 | Wogoman |
| 4,940,945 | A | 7/1990 | Littlejohn et al. |
| 4,970,145 | A | 11/1990 | Bennetto et al. |
| 4,975,647 | A | 12/1990 | Downer et al. |
| 4,999,582 | A | 3/1991 | Parks et al. |
| 4,999,632 | A | 3/1991 | Parks |
| 5,011,290 | A | 4/1991 | Terada et al. |
| 5,053,199 | A | 10/1991 | Keiser et al. |
| 5,108,564 | A | 4/1992 | Szuminsky et al. |
| 5,128,015 | A | 7/1992 | Szuminsky et al. |
| 5,160,980 | A | 11/1992 | Herpichboehm et al. |
| 5,179,005 | A | 1/1993 | Phillips et al. |
| 5,232,668 | A | 8/1993 | Grant et al. |
| 5,243,516 | A | 9/1993 | White |
| 5,246,858 | A | 9/1993 | Arbuckle et al. |
| 5,264,103 | A | 11/1993 | Yoshioka et al. |
| 5,269,891 | A | 12/1993 | Colin |
| 5,284,770 | A | 2/1994 | Adrian et al. |
| 5,288,636 | A | 2/1994 | Pollmann et al. |
| 5,312,762 | A | 5/1994 | Guiseppi-Elie |
| 5,352,351 | A | 10/1994 | White et al. |
| 5,366,609 | A | 11/1994 | White et al. |
| 5,371,687 | A | 12/1994 | Holmes et al. |
| 5,379,214 | A | 1/1995 | Arbuckle et al. |
| 5,385,846 | A | 1/1995 | Kuhn et al. |
| 5,395,504 | A | 3/1995 | Saurer et al. |
| 5,469,846 | A | 11/1995 | Khan |
| 5,508,171 | A | 4/1996 | Walling et al. |
| 5,508,203 | A | 4/1996 | Fuller et al. |
| 5,509,410 | A | 4/1996 | Hill et al. |
| 5,512,489 | A | 4/1996 | Girault et al. |
| 5,522,255 | A | 6/1996 | Neel et al. |
| 5,594,906 | A | 1/1997 | Holmes, II et al. |
| 5,686,659 | A | 11/1997 | Neel et al. |
| 5,710,622 | A | 1/1998 | Neel et al. |
| 5,789,664 | A | 8/1998 | Neel et al. |
| 5,792,944 | A | 8/1998 | Lennert et al. |
| 5,832,921 | A | 11/1998 | Lennert et al. |
| 5,841,023 | A | 11/1998 | Parker et al. |
| 5,942,102 | A | 8/1999 | Hodges et al. |
| 5,997,817 | A | 12/1999 | Crismore et al. |
| 6,121,050 | A | 9/2000 | Han |
| 6,153,069 | A | 11/2000 | Pottgen et al. |
| 6,287,451 | B1 | 9/2001 | Winarta et al. |
| 6,377,896 | B1 | 4/2002 | Sato et al. |
| 6,413,411 | B1 | 7/2002 | Pottgen et al. |
| 6,576,117 | B1 | 6/2003 | Iketaki et al. |
| 7,018,843 | B2 * | 3/2006 | Heller .............................. 436/95 |

FOREIGN PATENT DOCUMENTS

| | | |
|---|---|---|
| EP | 206218 | 12/1986 |
| EP | 230472 | 8/1987 |
| EP | 241309 | 10/1987 |
| EP | 255291 | 2/1988 |
| EP | 471986 | 2/1992 |
| EP | 0 537 761 | 4/1993 |
| JP | 59013948 | 1/1984 |
| JP | 63-111453 | 5/1988 |
| JP | 63-128252 | 5/1988 |
| JP | 2651278 | 12/1990 |
| JP | 5297039 | 11/1993 |
| JP | 7055859 | 3/1995 |
| JP | 07-067698 A | 3/1996 |
| JP | 08-020364 B | 3/1996 |
| WO | WO 91/09373 | 6/1991 |
| WO | 98/35225 | 8/1998 |
| WO | 99/28736 | 6/1999 |
| WO | 99/32881 | 7/1999 |
| WO | 99/60391 | 11/1999 |
| WO | 0157510 | 8/2001 |
| WO | WO 01/57510 | 8/2001 |

OTHER PUBLICATIONS

Muller, et al, "Influence of Hematocrit and Platelet Count on Impedance and Reactivity of Whole Blood for Electrical Aggregometry," Journal of Pharmacological and Toxicological Methods, vol. 34, pp. 17-22 (1995).

Preidel, et al, "In Vitro Measurements with Electrocatalytic Glucose Sensor in Blood," Biomed. Biochim. Acta, vol. 48, pp. 897-903 (1989).

Preidel, et al, "Glucose Measurements by Electrocatalytic Sensor in the Extracorporeal Blood Circulation of a Sheep," Sensors and Actuators B, vol. 2, pp. 257-263 (1990).

Saeger, et al, "Influence of Urea on the Glucose Measurement by Electrocatalytic Sensor in the Extracorporeal Blood Circulation of a Sheep," Biomed. Biochim. Acta, vol. 50, pp. 885-891 (1991).

Kasapbasioglu, et al, "An Impedance Based Ultra-Thin Platinum Island Film Glucose Sensor," Sensors and Actuators B, vol. 13-14, pp. 749-751 (1993).

Beyer, et al, "Development and Application of a New Enzyme Sensor Type Based on the EIS-Capacitance Structure for Bioprocess Control," Biosensors & Bioelectronics, vol. 9, pp. 17-21 (1994).

Mohri, et al, "Characteristic Response of Electrochemical Nonlinearity to Taste Compounds with a Gold Electrode Modified with 4-Aminobenzenethiol," Bull. Chem. Soc. Jpn., vol. 66, pp. 1328-1332 (1993).

Cardosi, et al, "The Realization of Electron Transfer from Biological Molecules to Electrodes," *Biosensors Fundamentals and Applications*, chapt. 15 (Turner, et al, eds., Oxford University Press, 1987).

Mell, et al, "Amperometric Response Enhancement of the Immobilized Glucose Oxidase Enzyme Electrode," Analytical Chemistry, vol. 48, pp. 1597-1601 (Sep. 1976).

Mell, et al, "A Model for the Amperometric Enzyme Electrode Obtained Through Digital Simulation and Applied to the Immobilized Glucose Oxidase System," Analytical Chemistry, vol. 47, pp. 299-307 (Feb. 1975).

Myland, et al, "Membrane-Covered Oxygen Sensors: An Exact Treatment of the Switch-on Transient," Journal of the Electrochemical Society, vol. 131, pp. 1815-1823 (Aug. 1984).

Bradley, et al, "Kinetic Analysis of Enzyme Electrode Response," Anal. Chem., vol. 56, pp. 664-667 (1984).

Koichi,"Measurements of Current-Potential Curves, 6, Cottrell Equation and its Analogs. What Can We Know from Chronoamperometry?" Denki Kagaku oyobi Kogyo Butsuri Kagaku, vol. 54, No. 6, pp. 471-475 (1986).

Williams, et al, "Electrochemical-Enzymatic Analysis of Blood Glucose and Lactate," Analytical Chemistry, vol. 42, No. 1, pp. 118-121 (Jan. 1970).

Gebhardt, et al, "Electrocatalytic Glucose Sensor," Siemens Forsch.-u. Entwickl.-Ber. Bd., vol. 12, pp. 91-95 (1983).

E. Weber, *Linear Transient Analysis*, John Wiley and Sons, N.Y., 1954, pp. 60-61, 72-73 and 172-173.

"Measurement Reagent for Urea Nitrogen", Toyobo Co., Ltd., Revised Nov. 1, 1997.

Hempstead, Michael R., et al., "Cottrell Filtration: Removal of Extraneous Currents From a Faradaic Signal," Journal Electroanal Chem., vol. 162, (1984) pp. 1-12.

English translation-in-part of description of medicine for external diagnosis produced by Toyobo Co., Ltd. and sold by Ono Pharmaceutical Co., Ltd., Nov. 1, 1997.

Office Action (translation-in-part) of JP Patent Application No. 542930/2003, May 29, 2007.

Adams, Ralph N., "Electrochemistry at Solid Electrodes", Marcel Dekker, Inc., 1969, pp. 50-61.

Bard et al., "Electrochemical Methods. Fundamentals and Applications", John Wiley & Sons, 1980, pp. 128-129, 143, and 370-428.

Kissinger et al., "Laboratory Techniques in Electroanalytical Chemistry", Marcel Dekker, Inc. 1984, pp. 56-59.

Steinlage, Ralph C., "College Algebra and Trigonometry", West Publishing Company, 1984, pp. 160-161, 168-169 and 172-173.

* cited by examiner

INSTRUMENT

CROSS-REFERENCE TO RELATED APPLICATIONS

This application is a continuation of U.S. Ser. No. 10/046,030 filed Nov. 7, 2001, now U.S. Pat. No. 7,018,843 issued Mar. 28, 2006. The disclosure of U.S. Ser. No. 10/046,030 is hereby incorporated herein by reference.

FIELD OF THE INVENTION

This invention relates to methods and apparatus for the determination of the concentrations of biologically significant components of bodily fluids. It is disclosed in the context of methods and apparatus for the determination of glucose concentration in blood, a blood fraction or a control, but is believed to be useful in other applications as well.

BACKGROUND OF THE INVENTION

Various methods and apparatus for the determination of the concentrations of medically significant components of body fluids are known. There are, for example, the methods and apparatus illustrated and described in the following listed references: U.S. Pat. Nos. 3,770,607; 3,838,033; 3,902,970; 3,925,183; 3,937,615; 4,005,002; 4,040,908; 4,086,631; 4,123,701; 4,127,448; 4,214,968; 4,217,196; 4,224,125; 4,225,410; 4,230,537; 4,260,680; 4,263,343; 4,265,250; 4,273,134; 4,301,412; 4,303,887; 4,366,033; 4,407,959; 4,413,628; 4,420,564; 4,431,004; 4,436,094; 4,440,175; 4,477,314; 4,477,575; 4,499,423; 4,517,291; 4,654,197; 4,671,288; 4,679,562; 4,682,602; 4,703,756; 4,711,245; 4,734,184; 4,750,496; 4,759,828; 4,789,804; 4,795,542; 4,805,624; 4,816,224; 4,820,399; 4,871,258; 4,897,162; 4,897,173; 4,919,770; 4,927,516; 4,935,106; 4,938,860; 4,940,945; 4,970,145; 4,975,647; 4,999,582; 4,999,632; 5,053,199; 5,011,290; 5,108,564; 5,128,015; 5,160,980; 5,232,668; 5,243,516; 5,246,858; 5,269,891; 5,284,770; 5,288,636; 5,312,762; 5,352,351; 5,366,609; 5,371,687; 5,379,214; 5,385,846; 5,395,504; 5,469,846; 5,508,171; 5,508,203; 5,509,410; 5,512,489; 5,522,255; 5,594,906; 5,686,659; 5,710,622; 5,789,664; 5,792,944; 5,832,921; 5,841,023; 5,942,102; and 5,997,817: WO98/35225; WO99/28736; and WO99/32881 and certain references cited in WO99/32881: German Patent Specification 3,228,542: European Patent Specifications: 206,218; 230,472; 241,309; 255, 291; and, 471,986: and, Japanese Published Patent Applications JP 63-128,252 and 63-111,453.

There are also the methods and apparatus described in: Talbott, et al, "A New Microchemical Approach to Amperometric Analysis," Microchemical Journal, Vol. 37, pp. 5-12 (1988); Morris, et al, "An Electrochemical Capillary Fill Device for the Analysis of Glucose Incorporating Glucose Oxidase and Ruthenium (III) Hexamine as Mediator, Electroanalysis," Vol. 4, pp. 1-9 (1992); Cass, et al, "Ferrocene-Mediated Enzyme Electrode for Amperometric Determination of Glucose," Anal. Chem., Vol. 56, pp. 667-671 (1984); Zhao, "Contributions of Suspending Medium to Electrical Impedance of Blood," Biochimica et Biophysica Acta, Vol. 1201, pp. 179-185 (1994); Zhao, "Electrical Impedance and Haematocrit of Human Blood with Various Anticoagulants," Physiol. Meas., Vol. 14, pp. 299-307 (1993); Muller, et al., "Influence of Hematocrit and Platelet Count on Impedance and Reactivity of Whole Blood for Electrical Aggregometry," Journal of Pharmacological and Toxicological Methods, Vol. 34, pp. 17-22 (1995); Preidel, et al, "In Vitro Measurements with Electrocatalytic Glucose Sensor in Blood," Biomed. Biochim. Acta, Vol. 48, pp. 897-903 (1989); Preidel, et al, "Glucose Measurements by Electrocatalytic Sensor in the Extracorporeal Blood Circulation of a Sheep," Sensors and Actuators B, Vol. 2, pp. 257-263 (1990); Saeger, et al, "Influence of Urea on the Glucose Measurement by Electrocatalytic Sensor in the Extracorporeal Blood Circulation of a Sheep," Biomed. Biochim. Acta, Vol. 50, pp. 885-891 (1991); Kasapbasioglu, et al, "An Impedance Based Ultra-Thin Platinum Island Film Glucose Sensor," Sensors and Actuators B, Vol. 13-14, pp. 749-751 (1993); Beyer, et al, "Development and Application of a New Enzyme Sensor Type Based on the EIS-Capacitance Structure for Bioprocess Control," Biosensors & Bioelectronics, Vol. 9, pp. 17-21 (1994); Mohri, et al, "Characteristic Response of Electrochemical Nonlinearity to Taste Compounds with a Gold Electrode Modified with 4-Aminobenzenethiol," Bull. Chem. Soc. Jpn., Vol. 66, pp. 1328-1332 (1993); Cardosi, et al, "The Realization of Electron Transfer from Biological Molecules to Electrodes," *Biosensors Fundamentals and Applications*, chapt. 15 (Turner, et al, eds., Oxford University Press, 1987); Mell, et al, "Amperometric Response Enhancement of the Immobilized Glucose Oxidase Enzyme Electrode," Analytical Chemistry, Vol. 48, pp. 1597-1601 (September 1976); Mell, et al, "A Model for the Amperometric Enzyme Electrode Obtained Through Digital Simulation and Applied to the Immobilized Glucose Oxidase System," Analytical Chemistry, Vol. 47, pp. 299-307 (February 1975); Myland, et al, "Membrane-Covered Oxygen Sensors: An Exact Treatment of the Switch-on Transient," Journal of the Electrochemical Society, Vol. 131, pp. 1815-1823 (August 1984); Bradley, et al, "Kinetic Analysis of Enzyme Electrode Response," Anal. Chem., Vol. 56, pp. 664-667 (1984); Koichi, "Measurements of Current-Potential Curves," 6, Cottrell Equation and its Analogs. "What Can We Know from Chronoamperometry?" Denki Kagaku oyobi Kogyo Butsuri Kagaku, Vol. 54, no. 6, pp. 471-5 (1986); Williams, et al, "Electrochemical-Enzymatic Analysis of Blood Glucose and Lactate," Analytical Chemistry, Vol. 42, no. 1, pp. 118-121 (January 1970); and, Gebhardt, et al, "Electrocatalytic Glucose Sensor," Siemens Forsch.-u. Entwickl.-Ber. Bd., Vol. 12, pp. 91-95 (1983).

The disclosures of these references are hereby incorporated herein by reference. This listing is not intended as a representation that a complete search of all relevant prior art has been conducted, or that no better references than those listed exist. Nor should any such representation be inferred.

The clinically significant index of blood glucose, as used in the diagnosis and management of diabetes, is its concentration in the serum, the clear fraction of whole blood after separation of red cells, white cells and plasma. The concentration is determined by any of a variety of chemical and electrochemical methods.

Typically, a predefined sample of serum is transferred from the blood collection receptacle to a reaction vessel in which reagents are combined to produce a chemical reaction whose product is proportional to the total amount of glucose contained in the sample. The product of the chemical reaction can be quantified by gauging optical or electrochemical changes in the reaction mixture, represented as electrical signals or numerical values in digital format. Internal measurement units so obtained, such as optical absorbency, microamperes, and so on, can be converted into reportable clinical units such as milligrams per deciliter or the like, by a blood glucose testing instrument calibration process performed as part of the overall clinical procedure. Internal instrument responses are measured on a series of serum-based reference standards, and the responses and corresponding concentration values are plotted graphically to produce a calibration curve, or fitted computationally to a mathematical function representing concentration in terms of an instrument's response. Advances in computing since the development of many of the known clinical methods have permitted performance of complex data processing and calculation functions directly in even the smallest hand-held instruments.

In a serum-based assay system, the translated glucose concentration values are reported directly in units desired by the clinician. The excluded blood fractions do not figure either in the measurement or the translation process. This is not the case for a system in which the sample is in the form of whole blood. The coexisting blood fractions may affect the reported values, either through physical or chemical interference with the measurement process per se or due to their physical displacement of serum in the sample volume. That is, because the wet chemistry measures total glucose in the sample, the reported serum concentrations will vary as the relative fraction of the serum component varies from sample to sample (usually from individual to individual). In practice, the principle interference is from the red and white blood cells.

For these and a variety of other reasons related to the manner in which blood glucose monitors and test strips are distributed, the calibration procedure for monitors is relatively complicated. Typically, calibration is performed in two steps. In the first step, a large number of test strips in multiple whole blood monitors measure a series of synthetic working standards having a range of predetermined concentrations. The standards are quite stable, and are available in relatively large quantities. The standards' values are used to construct (a) working relationship(s) between the monitors' responses and the standards' concentrations. This step provides a large number of determinations which are then pooled statistically for increased precision over the monitor and test strip populations.

Then, in the second step, instrument response measurements are performed on whole blood samples from a relatively smaller population of human donors, which are paired with glucose values determined by the reference serum methodology to adjust the working curve to yield true reportable values. This step accounts on a statistical basis for the unique properties of human blood. Thus, human donors provide, as they should, the ultimate basis for monitor results.

The decimal fraction of whole blood volume occupied by red cells is known as hematocrit. Hematocrit correction on whole blood determinations would not be necessary if hematocrit did not vary from person to person, because its effect could be taken into account in the calibration process by introducing whole blood samples into the instrument during calibration and relating their internally-measured numbers to corresponding serum values determined during the reference phase of the calibration process. However, hematocrit values can vary between about 0.2 for individuals who suffer from anemia and about 0.6 for newborns. Since a glucose determination is subject to about a one percent variation for each percent hematocrit variation, the resulting uncertainty in indicated glucose concentration would be clinically undesirable. Therefore, unless a glucose determination methodology is employed which is hematocrit-independent, for closest agreement with laboratory reference methods, individual determinations of glucose concentration must be compensated or corrected for hematocrit. This applies both to the donors whose blood is used during the calibration process and to the patients whose glucose concentrations are of interest to the clinician.

DISCLOSURE OF THE INVENTION

According to one aspect of the invention, a method is provided for determining the concentration of a first, medically significant component of a biological fluid or a control. The biological fluid or control includes a second component which affects the determination of the concentration of the first component. The method includes performing a first measurement on the biological fluid or control, which first measurement varies with both the concentration of the first component and at least one of the presence and concentration of the second component. The method further includes performing a second measurement on the biological fluid or control, which second measurement also varies with the at least one of the presence and concentration of the second component, to develop an indication of the at least one of the presence and concentration of the second component. The method further includes removing an amount representative of the indicated presence or concentration of the second component from the concentration of the first component indicated by the first measurement.

Illustratively according to this aspect of the invention, the biological fluid is blood or a blood fraction.

Further illustratively according to this aspect of the invention, the first component is glucose.

Additionally illustratively according to this aspect of the invention, the second component is blood cells.

Illustratively according to this aspect of the invention, the second measurement is of a largely glucose-insensitive measure of hematocrit.

Additionally illustratively according to this aspect of the invention, the first measurement is of a hematocrit-sensitive measure of glucose concentration.

Further illustratively according to this aspect of the invention, the method includes contacting the biological fluid or control with a reactant before performing the first measurement in order to permit a reaction to take place between one of the first and second components and the reactant.

Illustratively according to this aspect of the invention, the first and second measurements exhibit an interdependence between the concentration of the first component and the concentration of the second component.

Further illustratively according to this aspect of the invention, performing a first measurement on the biological fluid or control, which first measurement varies with both the concentration of the first component and at least one of the presence and concentration of the second component, includes performing measurements of a time-varying function $i_1(t)$ having the general form $$i_1(t) = M/\sqrt{t} + B$$

where t is time from initiating the measurement, M is the slope of a graph of the function and B is a value the function approaches as t becomes very large.

Additionally illustratively according to this aspect of the invention, performing a second measurement on the biological fluid or control, which second measurement varies primarily only with the at least one of the presence and concentration of the second component, to develop an indication of the at least one of the presence and concentration of the second component includes performing at least one measurement of a time-varying function $i_2(t)$, where t is time, t<some arbitrarily established time. $i_1(t)$ and $i_2(t)$ may both exist in the circuit such that the aggregate current i(t) at an output of the circuit is their sum, that is, $i(t) = i_1(t) + i_2(t)$ where the clocks which measure $i_1(t)$ and $i_2(t)$ are appropriately synchronized.

Illustratively according to this aspect of the invention, removing an amount representative of the indicated presence or concentration of the second component from the concentration of the first component indicated by the first measurement includes removing from the measurements of $i_1(t)$ the at least one measurement of $i_2(t)$.

According to another aspect of the invention, an apparatus is provided for determining the concentration of a first, medically significant component of a biological fluid or a control. The biological fluid or control includes a second component which affects the determination of the concentration of the first component. The apparatus includes a device for performing a first measurement on the biological fluid or control, which first measurement varies with both the concentration of the first component and at least one of the presence and concentration of the second component. The device further performs a second measurement on the biological fluid or control, which second measurement varies primarily only with the at least one of the presence and concentration of the second component to develop an indication of the at least one of the presence and concentration of the second component. The device further removes an amount representative of the indicated presence or concentration of the second component from the concentration of the first component indicated by the first measurement.

Illustratively, apparatus according to this aspect of the invention includes apparatus for determining the concentration of a first, medically significant component of blood, a blood fraction or a control.

Further illustratively, apparatus according to this aspect of the invention includes apparatus for performing the first measurement on the blood, blood fraction or control, which first measurement varies with both the concentration of glucose and the concentration of blood cells in the blood, blood fraction or control.

Additionally illustratively, apparatus according to this aspect of the invention includes apparatus for performing the second measurement on the blood, blood fraction or control, which second measurement varies primarily only with the concentration of blood cells in the blood, blood fraction or control.

Illustratively, apparatus according to this aspect of the invention includes apparatus for performing the second measurement of a largely glucose-insensitive measure of hematocrit.

Additionally illustratively, apparatus according to this aspect of the invention includes apparatus for performing the first measurement of a hematocrit-sensitive measure of glucose concentration.

Further illustratively, apparatus according to this aspect of the invention includes a reactant for contacting the biological fluid or control before performing the first measurement in order to permit a reaction to take place between one of the first and second components and the reactant.

Illustratively, apparatus according to this aspect of the invention includes apparatus for performing first and second measurements which relate a non-linear variation of the concentration of the first component with the concentration of the second component.

Further illustratively according to this aspect of the invention, the device for performing a first measurement on the biological fluid or control, which first measurement varies with both the concentration of the first component and at least one of the presence and concentration of the second component, includes a device for performing measurements of a time-varying function $i_1(t)$ having the general form $$i_1(t) = M\sqrt{t} + B$$

where t is time from initiating the measurement, M is the slope of a graph of the function and B is a value the function approaches as t becomes very large.

Additionally illustratively according to this aspect of the invention, the device for performing a second measurement on the biological fluid or control, which second measurement varies primarily only with the at least one of the presence and concentration of the second component to develop an indication of the at least one of the presence and concentration of the second component, includes performing at least one measurement of a time-varying function $i_2(t)$, where t is some arbitrarily established time.

Illustratively according to this aspect of the invention, the device for removing an amount representative of the indicated presence or concentration of the second component from the concentration of the first component indicated by the first measurement includes a device for removing from the measurements of $i_1(t)$ the at least one measurement of $i_2(t)$.

BRIEF DESCRIPTION OF THE DRAWINGS

The invention may best be understood by referring to the following detailed description and accompanying drawings which illustrate the invention. In the drawings.

DETAILED DESCRIPTION OF ILLUSTRATIVE EMBODIMENTS

This application teaches an instrument and associated chemical and mathematical methods by which glucose and hematocrit are determined on a single sample and a single test strip.

This application also teaches an instrument and methods by which a data stream from such an instrument's reaction sensor can be processed by internal computational apparatus in such a manner as to decompose the data into components separately representing hematocrit and glucose concentration which can then be individually calibrated to report clinical values. In this regard, it is not necessary in diabetes management to report hematocrit. It is only necessary to free the measurement of glucose concentration from the effect of hematocrit. However, there are believed to be applications for a hand-held instrument which reports both values, such as, for example, an emergency room, a battlefield, and so on. In such applications, numerical components separately representing glucose concentration and hematocrit can be individually calibrated and translated to report clinical values. And it is believed that the invention is useful in other systems besides glucose concentration and hematocrit. Using appropriate sensor technology, other analytes can be detected and their concentrations in a sample determined and reported.

The reaction dynamics may produce such an interaction between the two components that separating the results of the two may require solution of a pair of simultaneous equations by algebraic means or by regression analysis.

Illustratively according to the invention, the two measurements proceed essentially simultaneously in a single passage of the sample through the instrument.

The need to account for the interference of other species with the determination of the concentration of a species of interest in biological fluids is well-documented. Among the numerous proposals for accomplishing this objective are those described in WO99/32881 and certain references cited in WO99/32881. This application proposes another mechanism for accounting for the interference of other species in the determination of the concentration of a species of interest in biological fluids. Hematocrit is defined as the percentage of the blood's volume that is cells. In instruments of the general types described in the above references, hematocrit interferes with the determination of glucose concentration of blood. This invention relates to the substantially simultaneous determination of hematocrit and indicated glucose concentration, which then permits indicated glucose concentration to be corrected for hematocrit to provide a more accurate indication of glucose concentration.

Figure 6:
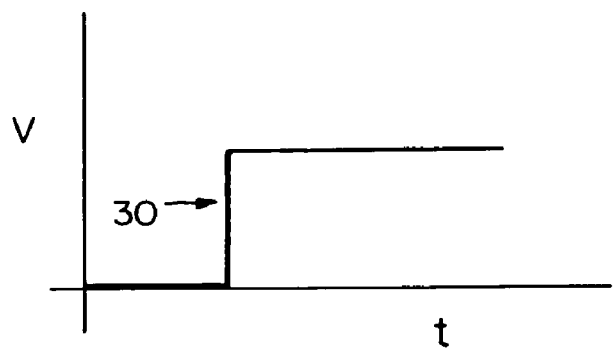
FIG. 6 illustrates a waveform useful in understanding the invention.

Glucose measurements on whole blood are intrinsically sensitive to hematocrit, principally, it is believed, through the volume exclusion effect. That is, the greater the hematocrit, the less glucose is available for the glucose oxidase reaction. Hence, in order to better the accuracy of such instruments, it is necessary to design the instruments and their glucose concentration determination algorithms around hematocrit, or to develop instruments and algorithms which measure hematocrit and compensate indicated glucose concentrations for the measured hematocrit, thus obtaining hematocrit-corrected glucose readings. An instrument 20 of the general type illustrated and described in U.S. Pat. Nos. 5,243,516; 5,288,636; 5,352,351; 5,385,846; and 5,508,171, for example, provides an incubation time, for example, ten seconds, for (a) reaction(s) to occur on a strip 22 of the general type illustrated and described in U.S. Pat. Nos. 5,243,516; 5,288,636; 5,352,351; 5,385,846; 5,508,171; and 5,997,817. Instrument 20 then applies across a pair of electrodes 26, 28 of strip 22 a step function voltage 30, FIG. 6, to circulate a current of electrons collected from, and returned to, ions produced by the glucose-glucose oxidase reaction and associated reactions. Current readings are made at intervals of, for example, a half second. A first reading, taken a very short time, for example, 0.02 sec., after application of the step function voltage 30, has previously been characterized by what were thought to be unpredictable artifacts. As a result, in prior art algorithms, such readings typically have not been used in the determination of glucose concentration.

Figure 1:
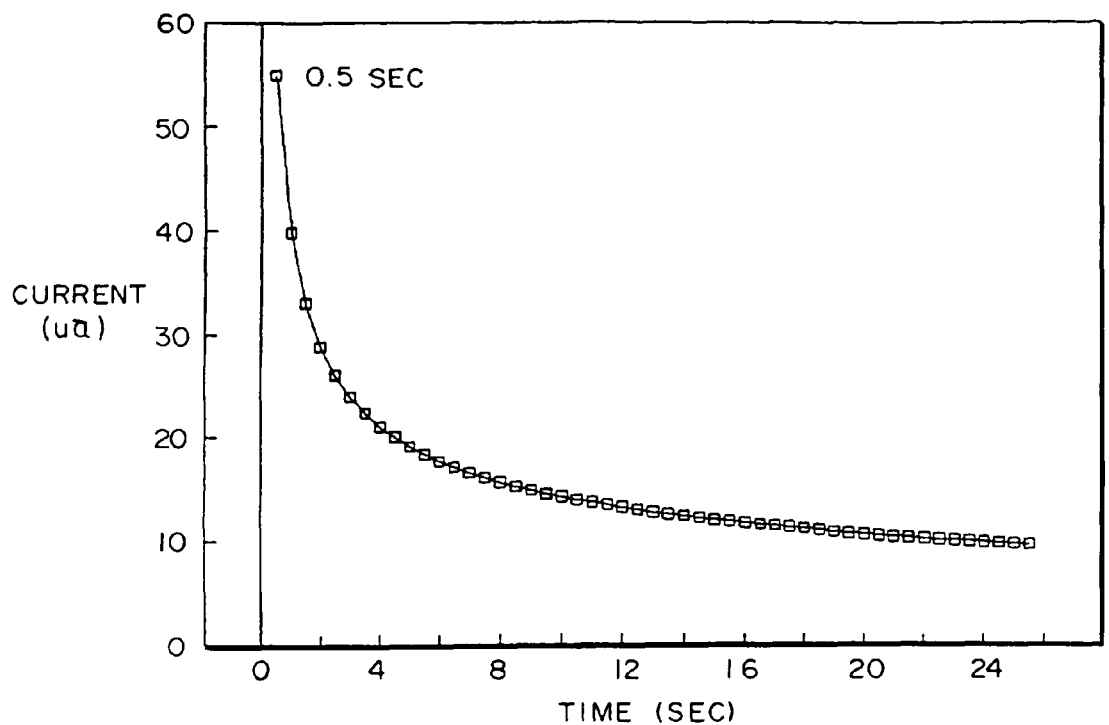
FIG. 1 illustrates a typical plot of current i versus time t for an instrument of the general type described.
Figure 2:
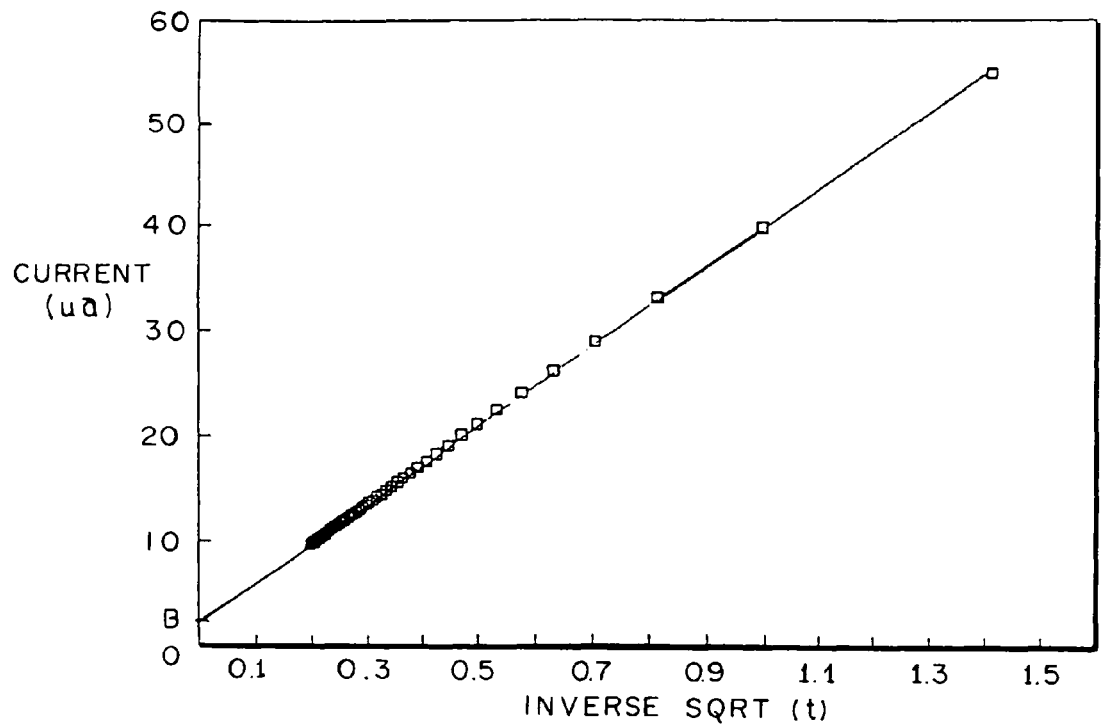
FIG. 2 illustrates a typical plot of i versus $1/\sqrt{t}$.

The Cottrell equation predicts that current will decrease as the inverse of the square root of time after the application of the step function voltage 30. M is directly proportional to analyte concentration. FIG. 1 illustrates a typical plot of Cottrell current i versus time t. FIG. 2 illustrates typical plots of i versus $1/\sqrt{t}$. Five sets of these data are illustrated in Table 1.

TABLE 1

| t | sample | | | | | $1/\sqrt{t}$ |
|---|---|---|---|---|---|---|
| | 1 | 2 | 3 | 4 | 5 | |
| 0.0 | 144.23 | 133.68 | 144.34 | 137.70 | 149.78 | |
| 0.5 | 22.07 | 20.30 | 22.06 | 18.97 | 22.88 | 1.41 |
| 1.0 | 16.15 | 14.94 | 16.06 | 13.78 | 16.60 | 1.00 |
| 1.5 | 13.46 | 12.55 | 13.34 | 11.48 | 13.83 | 0.82 |
| 2.0 | 11.86 | 11.11 | 11.75 | 10.13 | 12.16 | 0.71 |
| 2.5 | 10.75 | 10.10 | 10.65 | 9.24 | 11.03 | 0.63 |
| 3.0 | 9.94 | 9.37 | 9.88 | 8.66 | 10.19 | 0.58 |
| 3.5 | 9.33 | 8.78 | 9.27 | 8.17 | 9.52 | 0.53 |
| 4.0 | 8.80 | 8.29 | 8.75 | 7.80 | 8.99 | 0.50 |
| 4.5 | 8.40 | 7.93 | 8.36 | 7.49 | 8.56 | 0.47 |
| 5.0 | 8.03 | 7.62 | 7.99 | 7.21 | 8.19 | 0.45 |
| 5.5 | 7.69 | 7.34 | 7.68 | 7.00 | 7.85 | 0.43 |
| 6.0 | 7.44 | 7.07 | 7.44 | 6.78 | 7.58 | 0.41 |
| 6.5 | 7.20 | 6.85 | 7.16 | 6.60 | 7.33 | 0.39 |
| 7.0 | 6.98 | 6.64 | 6.98 | 6.45 | 7.14 | 0.38 |
| 7.5 | 6.80 | 6.49 | 6.76 | 6.26 | 6.93 | 0.37 |
| 8.0 | 6.61 | 6.30 | 6.61 | 6.14 | 6.74 | 0.35 |
| 8.5 | 6.43 | 6.18 | 6.46 | 6.05 | 6.59 | 0.34 |
| 9.0 | 6.27 | 6.03 | 6.31 | 5.93 | 6.44 | 0.33 |
| 9.5 | 6.18 | 5.90 | 6.18 | 5.83 | 6.31 | 0.32 |
| 10.0 | 6.02 | 5.81 | 6.06 | 5.74 | 6.16 | 0.32 |
| 10.5 | 5.90 | 5.69 | 5.91 | 5.62 | 6.07 | 0.31 |
| 11.0 | 5.81 | 5.60 | 5.82 | 5.56 | 5.94 | 0.30 |
| 11.5 | 5.72 | 5.51 | 5.69 | 5.46 | 5.85 | 0.29 |

Unless otherwise specified, in the tables and discussions that follow, current is measured in microamperes (µA), time in seconds (sec), and glucose concentrations in milligrams/deciliter (mg/dl). As will be appreciated, these plots are quite linear, and can be characterized by the equation:

$$i(t) = M/\sqrt{t} + B \quad (1)$$

where M is the slope of the Cottrell current curve and B is the asymptotic current, at $t=\infty$.

In the data studied, the B parameter was found to yield no independent correlation with glucose concentration, and considerably more variation; hence it was dropped from further consideration in the analyses.

Figure 3:
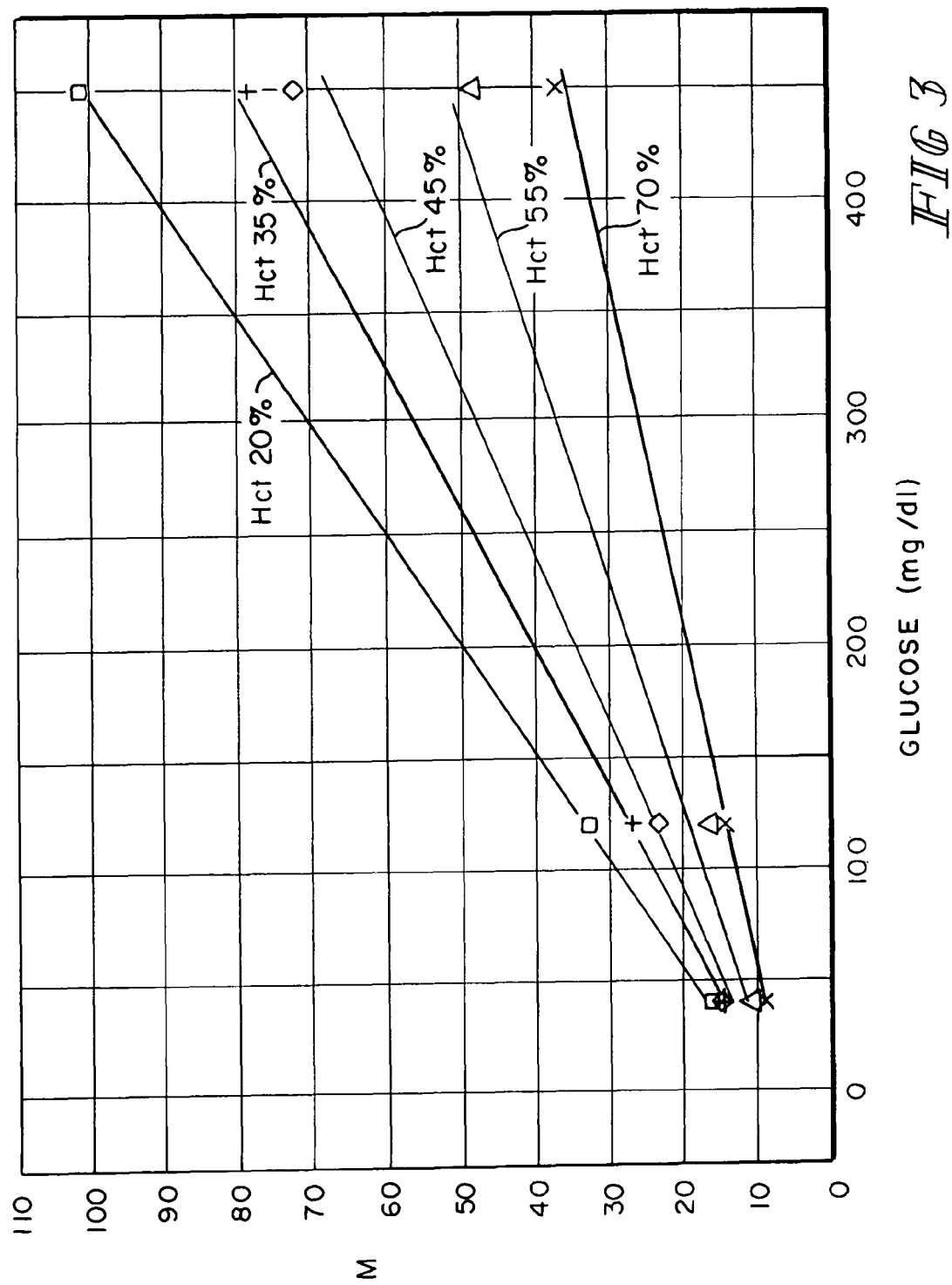
FIG. 3 illustrates plots of M, the slope of Cottrell current i(t) as a function of time t, versus glucose concentration at different hematocrits.

Although an assay for glucose could be based solely on the M parameter, a series of measurements with specially-prepared whole blood samples showed that for greater accuracy, hematocrit effects on indicated glucose concentration must be taken into account. FIG. 3 illustrates plots of M versus glucose concentration at different hematocrits for an illustrative set of data. The constant, or iso-, hematocrit contours form a manifold of separated, nearly straight lines that converge at a point near zero glucose concentration. The lines' slopes indicate relatively high sensitivity to variation in glucose concentration. However, there definitely is also hematocrit dependence. Given a measured M, the sought-after glucose concentration might fall on any line in the manifold, depending upon the hematocrit of the sample.

Figure 4:
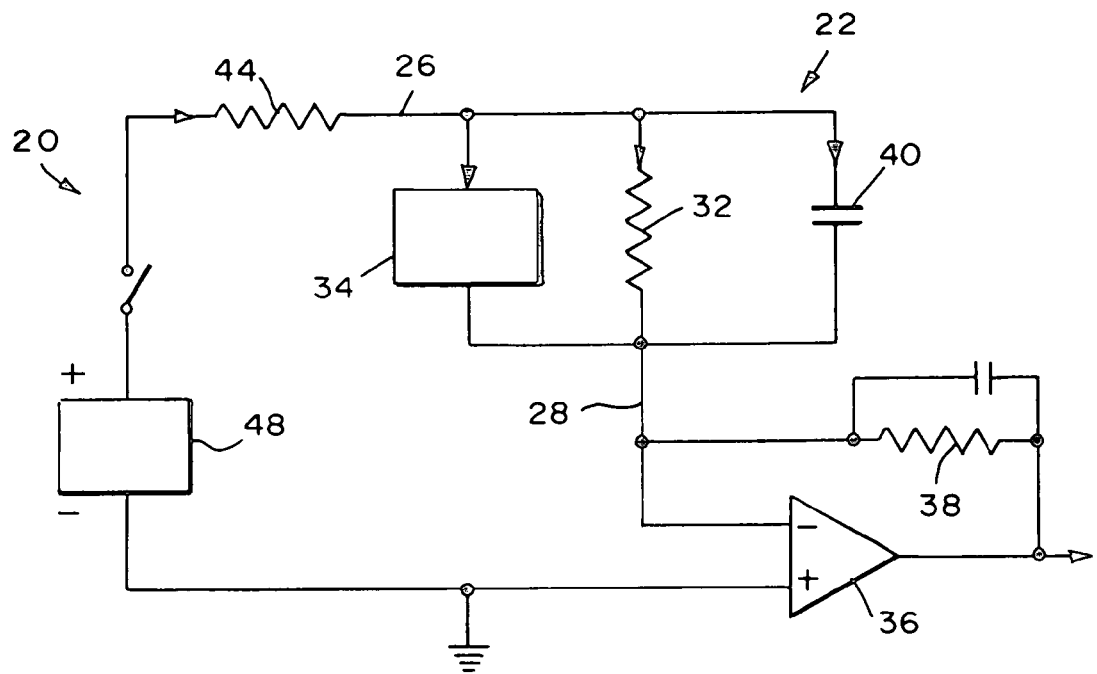
FIG. 4 illustrates an equivalent circuit model of an instrument and test strip of the general type described.

In order to learn whether a single measurement process that would be compatible with an instrument primarily designed to measure the Cottrell current could be configured to concurrently provide an index of hematocrit, the electrical properties of the strip and measuring circuit were studied in further detail. FIG. 4 illustrates an equivalent circuit model that models with a few conventional circuit elements the electrical performance of instrument 20 and strip 22. The circuit illustrated in FIG. 4 includes a resistor 32 that represents the ionic current flowing in the bulk of the reaction volume, as distinct from the Cottrell current source 34 that represents the electrochemical charge transfer and exhibits the $1/\sqrt{t}$ variability noted in the above equation. The sum of these two currents is provided to a current-to-voltage (i-v) converter 36, the output of which is a voltage across a feedback resistor 38. The output voltage of converter 36 is then sampled and analog-to-digital (A/D) converted for further processing by other circuitry (not shown) in the instrument 20.

In practice, for t>1 sec., the Cottrell current generator 34 and resistors 32 and 44 accurately represent the equivalent circuit. However, for a rapidly increasing voltage, such as the leading edge of a step function, the strip capacitance 40 acts as a transitory short circuit and Cottrell current cannot build up until the voltage across capacitance 40 is charged up, through resistor 44, to the step height. For the circuit parameters at hand, this time is less than a tenth of a second. Accordingly, for very short times (t<1 sec.), the capacitance 40 associated with strip 22 and sample 42 must also be included in the model, in parallel with the resistor 32 and the Cottrell current source 34. Following completion of the charge-transfer process, resistors 32 and 44 account for the residual current represented by the B parameter.

Figure 5:
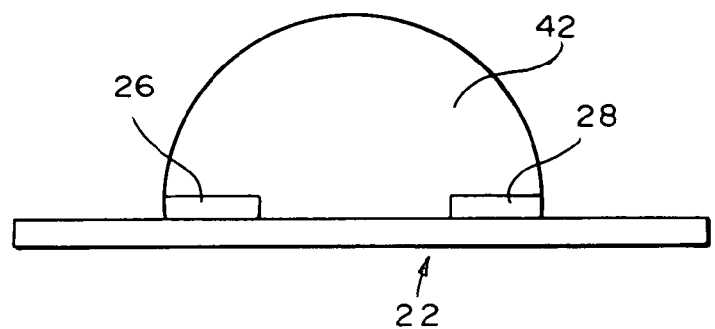
FIG. 5 illustrates a schematic view of a glucose test strip of the general type described, with an applied sample, looking outward from the strip port on an instrument of the general type described.

Capacitance 40 can be appreciated by referring to FIG. 5, a schematic view of strip 22 with an applied sample 42, looking outward from the strip 22 port on instrument 20, that is, along the strip 22 electrodes 26, 28 toward the applied sample 42. The electrodes 26, 28 of strip 22 form a pair of parallel plates 26, 28 having areas A, separated by a distance d. An illustratively somewhat hemispherical space above strip 22 and between the electrodes 26, 28 is filled with the sample 42 including whatever reagent(s), etc., are dissolved, suspended, or otherwise present, with or in the sample 42. Since blood is a composite material including two main components, plasma (the main liquid component of blood) and red blood cells (the main cellular, or solid, component of blood), the capacitance 40 should vary with hematocrit, to the extent that the dielectric properties of plasma and red blood cells differ. This expectation forms the basis of Fricke's equation:

$$\frac{(K - Ks)}{(K + S \times Ks)} = H \times \frac{(Kc - Ks)}{(Kc + S \times Ks)} \quad (2)$$

wherein: K=the composite dielectric constant of the sample 42; Ks=the dielectric constant of the serum component; Kc=the dielectric constant of the red blood cells; H=the hematocrit; and S=a so-called "shape factor" related to the architecture of the strip 22, illustratively about 1.8. The dielectric constant of whole blood is directly proportional to its hematocrit. Because the capacitance 40 of a strip 22 is directly proportional to the dielectric constant of its contents, equation (2) suggests that a determination of strip capacitance 40 would provide independent knowledge of the hematocrit of the sample.

Figure 7:
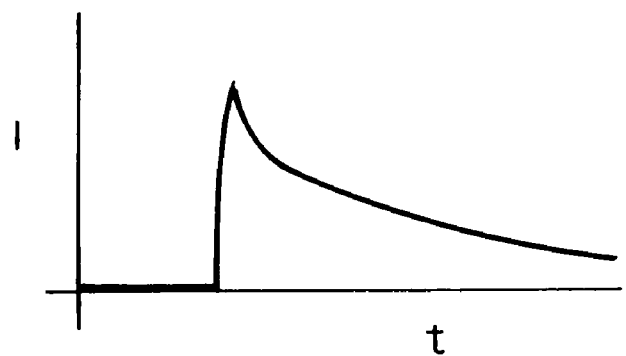
FIG. 7 illustrates a waveform useful in understanding the invention.
Figure 8:
FIG. 8 illustrates a waveform useful in understanding the invention.

Capacitance 40 can be quantified in a number of ways. For this application, the method involves utilizing the same hardware as an instrument designed to measure Cottrell current exclusively, while revising the associated software. Referring particularly to FIG. 7, if instrument 20 applies a step function voltage 30 across the strip 22 electrodes 26, 28, that voltage step 30 must charge the capacitance 40 of strip 22 and sample 42. As capacitance 40 is charged, the voltage across the strip electrodes 26, 28 asymptotically approaches a steady state value. The charging current spike has an initial value equal to the amplitude of the voltage step 30 divided by the internal resistance 44 of instrument 20, plus the leakage current of strip 22. Then, as the charge stored in capacitance 40 increases further, the current through strip 22 settles to the $1/\sqrt{t}$-related Cottrell current as described by the above equation. Thus, the current at any instant is the sum of these two, and any deficit between the actual current and the Cottrell current can be attributed to capacitance 40. FIG. 7 illustrates such a sum current trace. FIG. 8 illustrates the Cottrell current component calculated from t=0.5 second onward. D is the percent deficit between the sum current and the Cottrell current extrapolated from t=0.5 sec. backward toward t=0, and includes the current flow immediately after voltage is applied at t=, for example, 0.02 sec. D as a percentage of the total current is used because it is related to hematocrit, which is a percentage.

Figure 9:
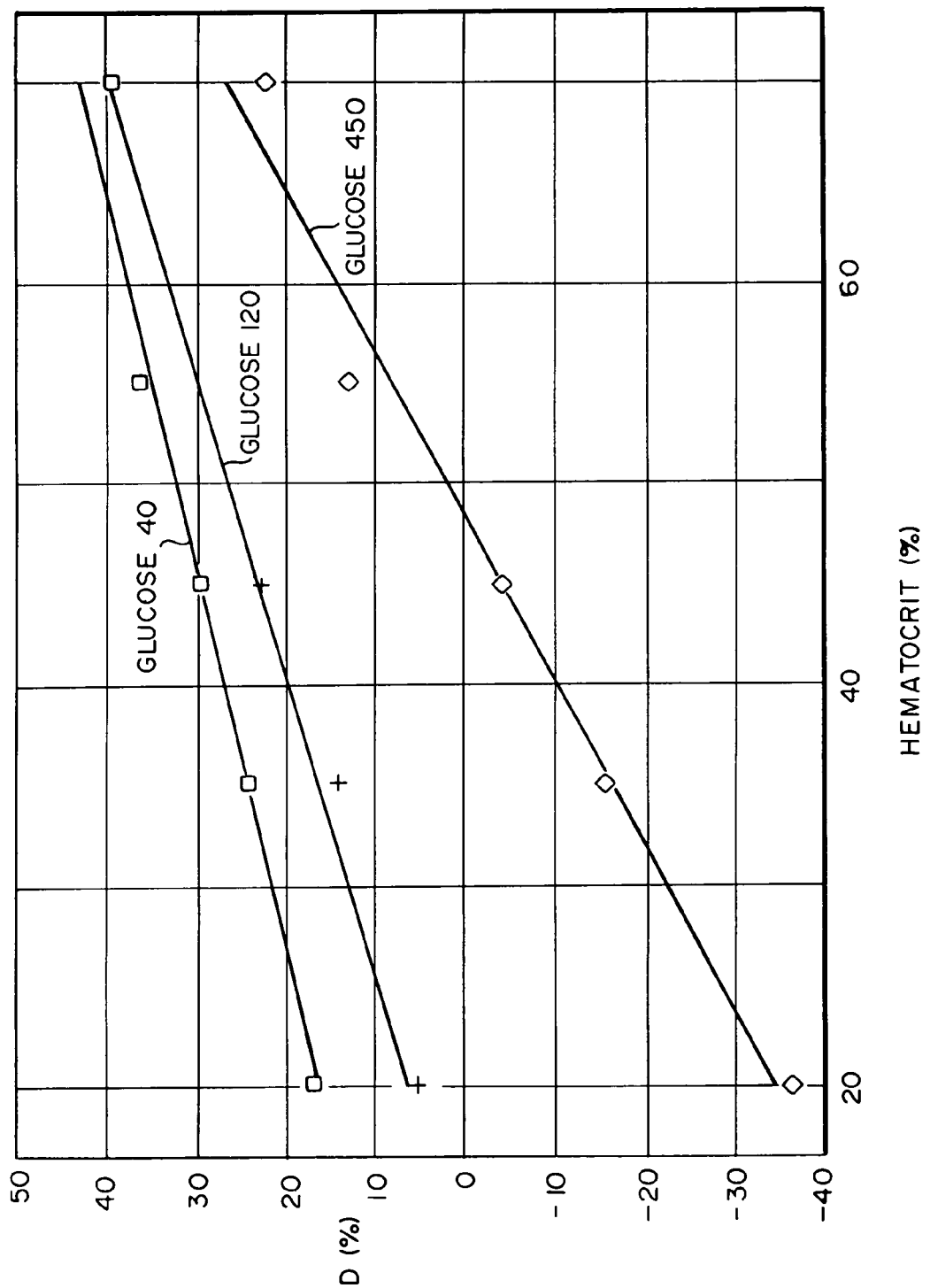
FIG. 9 illustrates plots of D, the percentage initial current deficit, versus hematocrit at some arbitrarily short time after application of a step function voltage to a circuit of the type illustrated in FIGS. 5-6; and, FIGS. 10 and 11 illustrate equivalent circuit models of an instrument and test strip of the general type described.

An investigation of the initial current spike was then undertaken. FIG. 9 illustrates plots of the percentage initial current deficit, hereinafter D, versus hematocrit at some arbitrarily short time after application of the step function voltage 30, again, illustratively t=0.02 sec. These plots are based upon the same set of data as the plots illustrated in FIG. 3. Each plot provides information on both glucose concentration and hematocrit. Table 2 illustrates how D is calculated for particular sets of data.

TABLE 2

|  | data group | | | | | mean of data groups | standard deviation of data groups | coefficients of variation of data groups |
| --- | --- | --- | --- | --- | --- | --- | --- | --- |
|  | 1 | 2 | 3 | 4 | 5 | | | |
| Cottrell current slope M at time t | 14.89 | 13.39 | 14.82 | 11.93 | 15.33 | 14.07 | 1.25 | 8.91 |
| Cottrell curve intercept B | 1.27 | 1.56 | 1.28 | 1.88 | 1.30 | 1.46 | 0.24 | 16.30 |
| measured i(t) − B | 142.96 | 132.12 | 143.06 | 135.82 | 148.48 | 140.49 | 5.80 | 4.13 |
| Cottrell component | 105.29 | 94.71 | 104.79 | 84.36 | 108.39 | 99.51 | 8.86 | 8.91 |
| Deficit D | 37.67 | 37.41 | 38.27 | 51.46 | 40.09 | 40.98 | 5.32 | 12.98 |
| D/(i(t) − B) × 100% | 26.35 | 28.32 | 26.75 | 37.89 | 27.00 | 29.26 | 4.36 | 14.91 |

Table 3 contains calculated values for M and D for each of the fifteen data points (three different glucose concentrations times five different hematocrits) in one run.

TABLE 3

| hematocrit | glucose concentration | | | | | |
| --- | --- | --- | --- | --- | --- | --- |
| | 40 D | 40 M | 120 D | 120 M | 450 D | 450 M |
| 20 | 17.1 | 16.0 | 5.4 | 32.9 | −36.4 | 101.2 |
| 35 | 24.3 | 14.4 | 14.2 | 27.0 | −15.3 | 78.4 |
| 45 | 29.8 | 14.6 | 22.7 | 23.3 | −3.9 | 71.9 |
| 55 | 36.4 | 10.8 | 35.6 | 16.6 | 12.9 | 48.5 |
| 70 | 39.4 | 9.4 | 40.1 | 14.4 | 22.1 | 37.0 |

The relationships among M, glucose concentration and hematocrit can be developed from the contents of Table 3. To accomplish this, M in Table 3 is regressed on a suitable set of variables. First, the shapes of the curves in FIG. 3 suggest a relationship of the form $$M = m_0 + m_1 \times h + m_2 \times g + m_3 \times h \times g \quad (3)$$

where h=(hematocrit−0.45) and g=(glucose concentration−120). Similarly, study of the curves of FIG. 9 suggest a relationship for D having the form $$D = d_0 + d_1 \times h + d_2 \times g + d_3 \times h \times g. \quad (4)$$

Regression analyses on these two equations yield the following values for the constants: $m_0$=23.33; $m_1$=−37.83; $m_2$=0.1333; $m_3$=−0.2843; $d_0$=23.14; $d_1$=66.54; $d_2$=−0.0823; and, $d_3$=0.1669. These regression parameters $m_0$, $m_1$, $m_2$, $m_3$ and $d_0$, $d_1$, $d_2$, $d_3$ represent this database. That is, given a new sample taken from the same sample universe, and of known h and g values, the corresponding M and D values, measured on the same reagent lot and monitor instruments, could be predicted using these parameters in equations (3) and (4). Alternatively, as would be the case in practice, the equations (3) and (4) can be inverted, numerically or algebraically, to yield the glucose and hematocrit values for a pair of M, D values measured on a sample whose glucose and hematocrit values were unknown.

This analysis of strip 22 with applied sample 42 was developed based on the step function response of the measurement strip to isolate the capacitance 40. Whereas $i_2(t)$, the charging of the relatively small strip 22 capacitance 40 through the relatively low output resistance 44 is essentially complete in the first second, $i_1(t)$, the Cottrell current, persists for several seconds, which permits determination of the Cottrell current trace and extrapolation back in time to extract a single value of $i_2(t)$ from the sum current i(t). Other means known to circuit designers could be employed.

Figure 10:
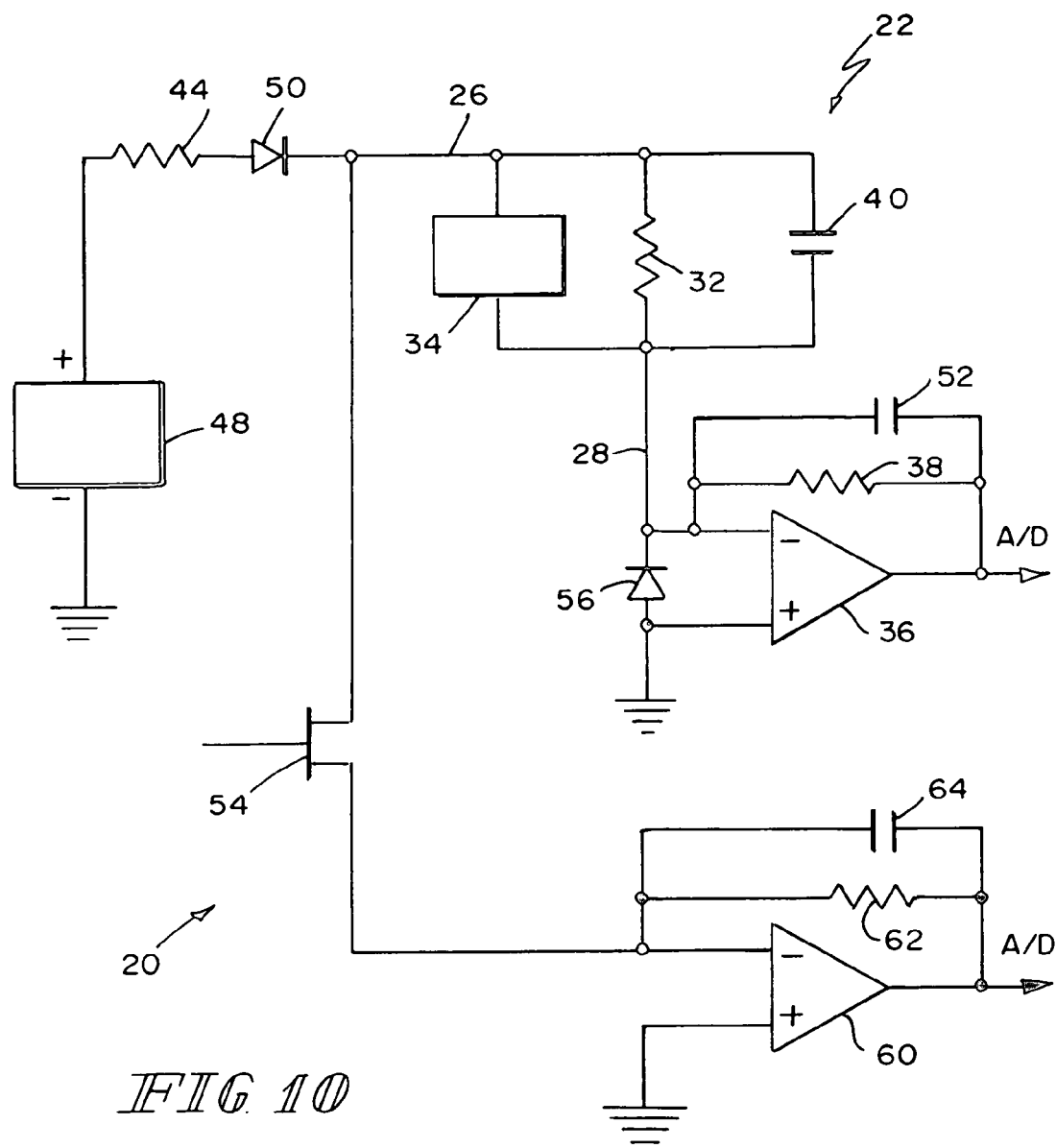
Figure 11:
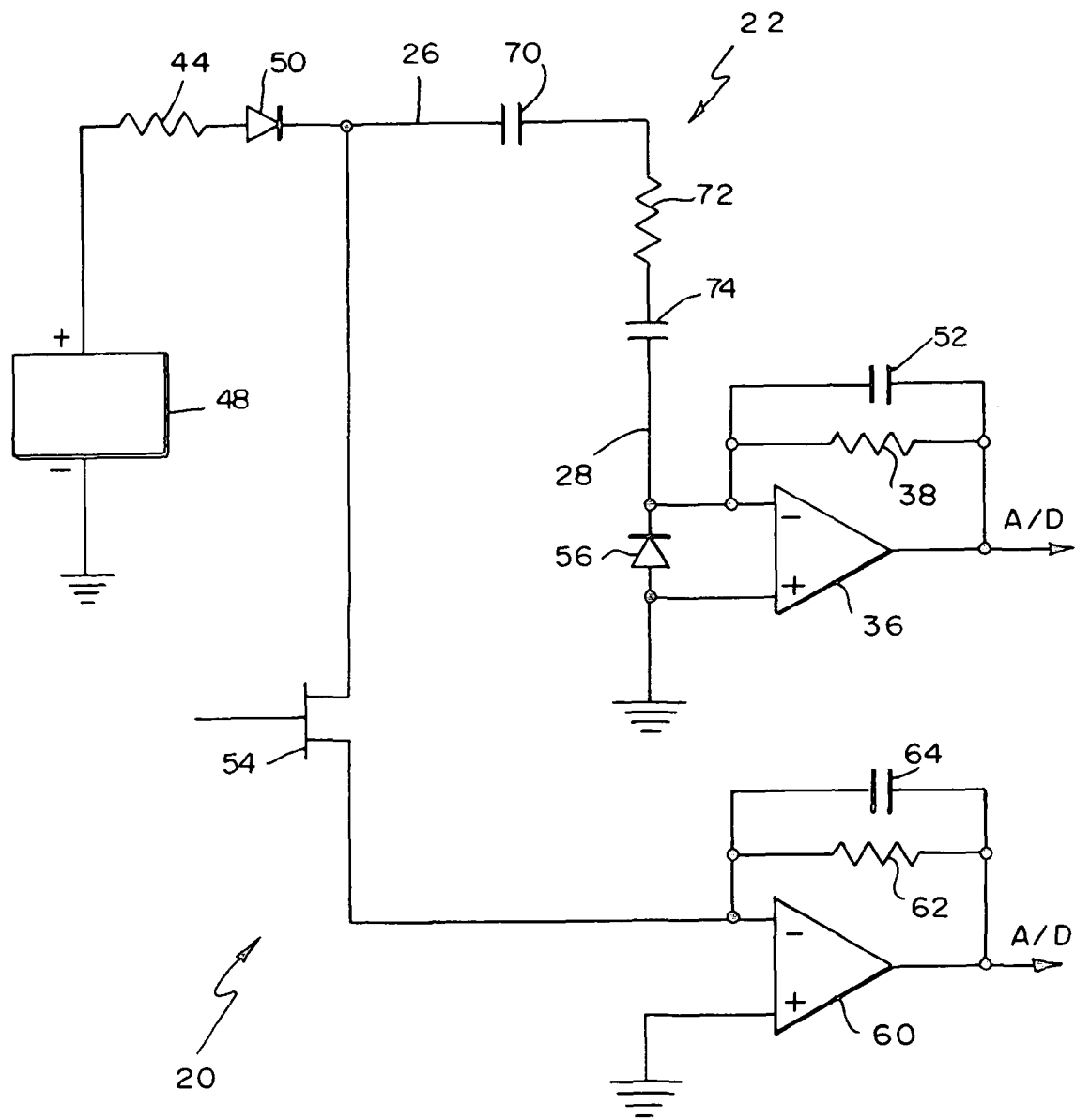

For example, the circuit illustrated in FIG. 10 provides an alternative technique for analyzing the behavior of the strip 22/applied sample 42 that is compatible with the measurement parts of instrument 20 and strip 22, but circuit and software are revised to give a longer measurement interval for the capacitance. In the circuit realization illustrated in FIG. 10, during reading of the current between the electrodes 26, 28 of strip 22, a programmed voltage source 48 and internal resistance 44 are coupled in series between the instrument 20 ground, or common, terminal and the anode of a blocking diode 50. The cathode of blocking diode 50 is coupled through the parallel combination of Cottrell current generator 34, asymptotic current resistor 32 and capacitor 40 to the inverting, or −, input terminal of a differential amplifier 36. The − input terminal of amplifier 36 is coupled through a parallel RC feedback circuit including a feedback resistor 38 and a feedback capacitor 52, to its output terminal. The measurement of the current through the strip 22 proceeds as described above, and the output from amplifier 36 is sampled and A/D converted for further processing by the instrument 20.

Then, after the measurement cycle of the current through the strip 22, the strip 22 capacitance 40 is discharged to determine the charge accumulated on it during the current measurement phase. The programmed voltage source 48 is stilled, and a Field Effect Transistor (FET) switch 54 is turned on. When this condition occurs, ground is coupled through a bypass diode 56 to the parallel combination of the Cottrell current generator 34, resistor 32 and capacitor 40 and through the FET switch 54 to the − input terminal of an amplifier 60. The − input terminal of amplifier 60 is coupled through the parallel combination of a feedback resistor 62 and a feedback capacitor 64 to its output terminal. The − input terminal of amplifier 60 is also coupled through the feedback resistor 62/feedback capacitor 64 parallel combination to its output. The output from amplifier 60 is sampled and A/D converted for further processing by the instrument 20.

The programmed voltage source 48, internal resistance 44, blocking diode 50, bypass diode 56, amplifiers 36, 60, and their associated feedback resistors 38, 62, and capacitors 52, 64, and FET switch 54 are, of course, within the instrument 20. Strip 22 is modeled by the Cottrell current source 34, resistor 32 and capacitor 40 coupled in parallel between the cathode of blocking diode 50 and the cathode of bypass diode 56. During current measurement, FET switch 54 is off, isolating the strip 22 circuit model from the inverting (−) input terminal of amplifier 60. When current measurement is complete, the FET switch 54 is turned on, and the strip 22 capacitance 40 is measured through instrument 20's amplifier 60, the output of which can be A/D converted by instrument 20 and used to calculate capacitance 40.

Both embodiments discussed above obtain hematocrit-free glucose determinations or simultaneous determinations of both hematocrit and glucose, making use of their relationships to circuit elements in the equivalent circuit of FIG. 4. This is accomplished by measuring some feature of the output current of the circuit subject to step function input voltage 38 of a waveform that rapidly rises to a steady state value which is maintained for the duration of the measurement interval. The current amplitude over time, normalized to that of the step, is known as the indicial admittance. See, for example, E. Weber, *Linear Transient Analysis*, John Wiley and Sons, N.Y., 1954. Such indicial admittance completely characterizes the electrical properties of the circuit, and can be transformed mathematically to resolve values for the individual circuit elements.

This resolution method can bypass such a laborious transformation by temporal separation of the two current contributors. Whereas $i_2(t)$, the charging of the relatively small strip 22 capacitance 40 through the relatively low output resistance 44 is essentially complete in the first second, $i_1(t)$, the Cottrell current, persists for several seconds, which permits determination of the Cottrell current trace and extrapolation back in time to extract a single value of $i_2(t)$ from the sum current i(t).

Because of the parallel nature of the circuit, $i_2(t)$ is the indicial admittance of the strip and sample, a single point of which has sufficed to illustrate the principle of identifying separate analytes with separate circuit elements.

*Linear Transient Analysis*, referenced above, teaches at page 173 that a circuit's properties can be equivalently characterized by its impedance function, the ratio of amplitude of an applied sinusoidal voltage V(ω) to the complex circuit current I(ω), V/I as a function of frequency ω. The temporal and frequency representations are related by a set of integral equations, also taught at *Linear Transient Analysis*, page 73, that are readily reduced to transform between them. Thus, the measurement could be made by using a constant-amplitude, swept frequency, sinusoidal voltage generator, and recording the amplitude and phase of the output sinusoidal current, the two methods being electrically entirely equivalent. As above, various indices of the real and imaginary components of the impedance function can be extracted which, when regressed on assay values in a calibration reference set, will yield relations for the assay values of patient samples.

The invention claimed is:

1. A method for determining the concentration of a first, medically significant component of a biological fluid or a control, the biological fluid or control including a second component which affects the determination of the concentration of the first component, the method including performing a first measurement of a time-varying function $i_1(t)$ on the biological fluid or control which first measurement varies with both the concentration of the first component and at least one of the presence and concentration of the second component, $i_1(t)$ having the general form $$i_1(t)=M/\mathrm{sqrt}(t)+B$$

where t is time from initiating the measurement, M is the slope of a graph of the function and B is a value the function approaches as t becomes very large, performing a second measurement on the biological fluid or control which second measurement has the form of a time-varying function $i_2(t)$, where t is time, t<some arbitrarily established time, $i_2(t)$ varying primarily only with the at least one of the presence and concentration of the second component to develop an indication of the at least one of the presence and concentration of the second component, and removing an amount representative of the indicated presence or concentration of the second component from the concentration of the first component indicated by the first measurement.

2. The method of claim 1 wherein the biological fluid is blood or a blood fraction.

3. The method of claim 1 wherein the first component is glucose.

4. The method of claim 1 wherein the second component is blood cells.

5. The method of claim 1 further including contacting the biological fluid or control with a reactant before performing the first measurement.

6. The method of claim 5 wherein the biological fluid is blood or a blood fraction.

7. The method of claim 5 wherein the first component is glucose.

8. The method of claim 5 wherein the second component is blood cells.

9. The method of claim 5 wherein the first and second measurements exhibit an interdependence between the concentration of the first component and the concentration of the second component.

10. The method of claim 9 wherein the biological fluid is blood or a blood fraction.

11. The method of claim 9 wherein the first component is glucose.

12. The method of claim 9 wherein the second component is blood cells.

13. The method of claim 1 wherein the first and second measurements exhibit an interdependence between the concentration of the first component and the concentration of the second component.

14. The method of claim 13 wherein the biological fluid is blood or a blood fraction.

15. The method of claim 13 wherein the first component is glucose.

16. The method of claim 13 wherein the second component is blood cells.

17. Apparatus for determining the concentration of a first, medically significant component of a biological fluid or a control, the biological fluid or control including a second component which affects the determination of the concentration of the first component, the apparatus including a device for performing a first measurement of a time-varying function $i_1(t)$ on the biological fluid or control which first measurement varies with both the concentration of the first component and at least one of the presence and concentration of the second component, $i_1(t)$ having the general form $$i_1(t)=M/\mathrm{sqrt}(t)+B$$

where t is time from initiating the measurement, M is the slope of a graph of the function and B is a value the function approaches as t becomes very large, the device further performing a second measurement of a time-varying function $i_2(t)$ of the biological fluid or control, where t is time, t<some arbitrarily established time, which second measurement varies primarily only with the at least one of the presence and concentration of the second component to develop an indication of the at least one of the presence and concentration of the second component, and the device further removing an amount representative of the indicated presence or concentration of the second component from the concentration of the first component indicated by the first measurement.

18. The apparatus of claim 17 wherein the device determines the concentration of a first, medically significant component of blood, a blood fraction or a control.

19. The apparatus of claim 17 further including a reactant for contacting the biological fluid or control before performing the first measurement.

20. The apparatus of claim 19 wherein the device determines the concentration of a first, medically significant component of blood, a blood fraction or a control.

21. The apparatus of claim 19 wherein the device performs first and second measurements which exhibit an interdependence between the concentration of the first component and the concentration of the second component.

22. The apparatus of claim 21 wherein the device determines the concentration of a first, medically significant component of blood, a blood fraction or a control.

23. The apparatus of claim 22 wherein the device performs the second measurement on the blood, blood fraction or control which second measurement varies primarily only with the concentration of blood cells in the blood, blood fraction or control.

24. The apparatus of claim 17 wherein the device performs first and second measurements which exhibit an interdependence between the concentration of the first component and the concentration of the second component.

25. The apparatus of claim 24 wherein the device determines the concentration of a first, medically significant component of blood, a blood fraction or a control.

26. The apparatus of claim 24 wherein the device performs the second measurement on the blood, blood fraction or control which second measurement varies primarily only with the concentration of blood cells in the blood, blood fraction or control.

27. A method for determining the concentration of a first, medically significant component of a biological fluid or a control, the biological fluid or control including a second component which affects the determination of the concentration of the first component, the method including performing a first measurement of a time-varying function $i_1(t)$ of the biological fluid or control, $i_1(t)$ varying with both the concentration of the first component and at least one of the presence and concentration of the second component, $i_1(t)$ having the general form $$i_1(t)=M/\mathrm{sqrt}(t)+B$$

where t is time from initiating the measurement, M is the slope of a graph of the function and B is a value the function approaches as t becomes very large, performing a second measurement on the biological fluid or control which second measurement also varies with the at least one of the presence and concentration of the second component to develop an indication of the at least one of the presence and concentration of the second component, and removing an amount representative of the indicated presence or concentration of the second component from the concentration of the first component indicated by the first measurement.

28. The method of claim 27 wherein the biological fluid is blood or a blood fraction.

29. The method of claim 27 wherein the first component is glucose.

30. The method of claim 27 wherein the second component is blood cells.

31. The method of claim 27 further including contacting the biological fluid or control with a reactant before performing the first measurement.

32. The method of claim 31 wherein the biological fluid is blood or a blood fraction.

33. The method of claim 31 wherein the first component is glucose.

34. The method of claim 31 wherein the second component is blood cells.

35. The method of claim 31 wherein the first and second measurements exhibit an interdependence between the concentration of the first component and the concentration of the second component.

36. The method of claim 35 wherein the biological fluid is blood or a blood fraction.

37. The method of claim 36 wherein the first component is glucose.

38. The method of claim 36 wherein the second component is blood cells.

39. The method of claim 27 wherein the first and second measurements exhibit an interdependence between the concentration of the first component and the concentration of the second component.

40. The method of claim 39 wherein the biological fluid is blood or a blood fraction.

41. The method of claim 39 wherein the first component is glucose.

42. The method of claim 39 wherein the second component is blood cells.

43. Apparatus for determining the concentration of a first, medically significant component of a biological fluid or a control, the biological fluid or control including a second component which affects the determination of the concentration of the first component, the apparatus including a device for performing a first measurement of a time-varying function $i_1(t)$ of the biological fluid or control, $i_1(t)$ varying with both the concentration of the first component and at least one of the presence and concentration of the second component, $i_1(t)$ having the general form $$i_1(t)=M/\mathrm{sqrt}(t)+B$$

where t is time from initiating the measurement, M is the slope of a graph of the function and B is a value the function approaches as t becomes very large, the device further performing a second measurement on the biological fluid or control which second measurement varies primarily only with the at least one of the presence and concentration of the second component to develop an indication of the at least one of the presence and concentration of the second component, and the device further removing an amount representative of the indicated presence or concentration of the second component from the concentration of the first component indicated by the first measurement.

44. The apparatus of claim 43 wherein the device determines the concentration of a first, medically significant component of blood, a blood fraction or a control.

45. The apparatus of claim 44 wherein the device performs the second measurement on the blood, blood fraction or control which second measurement varies primarily only with the concentration of blood cells in the blood, blood fraction or control.

46. The apparatus of claim 43 further including a reactant for contacting the biological fluid or control before performing the first measurement.

47. The apparatus of claim 46 wherein the device determines the concentration of a first, medically significant component of blood, a blood fraction or a control.

48. The apparatus of claim 47 wherein the device performs the second measurement on the blood, blood fraction or control which second measurement varies primarily only with the concentration of blood cells in the blood, blood fraction or control.

49. The apparatus of claim 46 wherein the device performs first and second measurements which exhibit an interdependence between the concentration of the first component and the concentration of the second component.

50. The apparatus of claim 49 wherein the device determines the concentration of a first, medically significant component of blood, a blood fraction or a control.

51. The apparatus of claim 50 wherein the device performs the second measurement on the blood, blood fraction or control which second measurement varies primarily only with the concentration of blood cells in the blood, blood fraction or control.

52. The apparatus of claim 43 wherein the device performs first and second measurements which exhibit an interdependence between the concentration of the first component and the concentration of the second component.

53. The apparatus of claim 52 wherein the device determines the concentration of a first, medically significant component of blood, a blood fraction or a control.

54. The apparatus of claim 53 wherein the device performs the second measurement on the blood, blood fraction or control which second measurement varies primarily only with the concentration of blood cells in the blood, blood fraction or control.

* * * * *